United States Patent
Shalaev et al.

(10) Patent No.: US 6,764,993 B2
(45) Date of Patent: Jul. 20, 2004

(54) USE OF O-VANILLIN AND O-VANILLIN/TROLOX COMBINATIONS

(75) Inventors: Evgenyi Y. Shalaev, Old Lyme, CT (US); Renuka D. Reddy, Waterford, CT (US); Roger N. Kimball, Waterford, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/805,016

(22) Filed: Mar. 12, 2001

(65) Prior Publication Data

US 2001/0049354 A1 Dec. 6, 2001

Related U.S. Application Data

(60) Provisional application No. 60/189,101, filed on Mar. 14, 2000.

(51) Int. Cl.$^7$ .................. A61K 47/08; A61K 38/21; A61K 38/22; A61K 38/39
(52) U.S. Cl. .................. 514/2; 422/22; 426/240; 514/456; 514/699; 530/344; 530/412
(58) Field of Search .................. 422/1, 21, 22, 422/23, 24; 426/240; 424/85.1, 130.1, 176.1; 514/2, 3, 8, 12, 21, 456, 699, 917; 530/300, 305, 344, 350, 351, 356, 357, 364, 370.1, 412

(56) References Cited

U.S. PATENT DOCUMENTS

| | | | |
|---|---|---|---|
| 3,986,980 A | 10/1976 | Cort | 426/545 |
| 4,714,609 A * | 12/1987 | Carden | 514/938 |
| 5,015,627 A | 5/1991 | Lindsey et al. | 514/12 |
| 5,198,422 A * | 3/1993 | Clark et al. | 514/12 |
| 5,730,933 A * | 3/1998 | Peterson | 422/22 |
| 5,789,396 A * | 8/1998 | Blank et al. | 514/159 |
| 5,811,083 A * | 9/1998 | Pelle et al. | 424/59 |
| 5,840,734 A * | 11/1998 | Bernstein | 514/315 |
| 5,977,068 A | 11/1999 | Tyle et al. | 514/12 |

FOREIGN PATENT DOCUMENTS

| WO | WO 9422484 | 10/1994 | A61K/47/48 |
|---|---|---|---|
| WO | WO 0000507 | 1/2000 | C07K/1/107 |

OTHER PUBLICATIONS

B. D. Reid, PDA J. Pharm. Sci. and Tech., 49 (2), 83–89 (1995).
G. P. Jacobs, J. Biomaterials App., 10, 59–95 (1995).
N.G.S. Gopal, Radiat. Phys. Chem., 12, 35–50 (1978).
Soebianto, et al., Polymer Degradation and Stability, 50, 203–210 (1995).
Klemchuk, Radiat. Phys. Chem., 41. 165–172 (1993).
Bisby, et al., Biochem. Biophys. Res. Comm., 119, 245–251 (1984).
Richaed J. Lewis, Sr., Hawley's Condensed Chemical Dictionary, Fourteenth Edition, p. 949 and p. 1148, ( not dated).

* cited by examiner

Primary Examiner—Jeffrey Edwin Russel
(74) Attorney, Agent, or Firm—Peter C. Richardson; Gregg C. Benson; Carmella A. O'Gorman

(57) ABSTRACT

The invention provides methods of protecting solid-state proteins from the effects of ionizing radiation which comprise combining the protein with a radiation-protecting amount of a methoxysalicylaldehyde derivative, preferably 3-methoxysalicylaldehyde; radiation-protecting amounts of a methoxysalicylaldehyde derivative, preferably 3-methoxysalicylaldehyde, and 6-hydroxy-2,5,7,8-tetramethylchroman-2-carboxylic acid; or radiation-protecting amounts of a methoxysalicylaldehyde derivative, preferably 3-methoxysalicylaldehyde and isopropanol, prior to exposing the protein to ionizing radiation. The invention further provides radiation-resistant pharmaceutical formulations comprising a protein and a methoxysalicylaldehyde derivative, preferably 3-methoxysalicylaldehyde; a protein and a combination of a methoxysalicylaldehyde derivative, preferably 3-methoxysalicylaldehyde, and 6-hydroxy-2,5,7,8-tetramethylchroman-2-carboxylic acid; or a protein and a combination of a methoxysalicylaldehyde derivative, preferably 3-methoxysalicylaldehyde and isopropanol. The invention still further provides a composition comprising a combination of a methoxysalicylaldehyde derivative, preferably 3-methoxysalicylaldehyde, and 6-hydroxy-2,5,7,8-tetramethylchroman-2-carboxylic acid, and for the use of such composition in pharmaceutical formulations as a radioprotectant.

21 Claims, No Drawings

US 6,764,993 B2

USE OF O-VANILLIN AND O-VANILLIN/TROLOX COMBINATIONS

CROSS REFERENCE TO RELATED APPLICATION

This application claims the benefit of U.S. Provisional Application No. 60/189,101 filed Mar. 14, 2000.

BACKGROUND OF THE INVENTION

The instant invention relates to the use of methoxysalicylaldehyde derivatives, preferably o-vanillin, and to methoxysalicylaldehyde derivatives, preferably o-vanillin, in combination with Trolox® or isopropanol, in protecting solid-state proteins from the effects of ionizing radiation. The invention further relates to radiation-resistant formulations comprising solid-state proteins and methoxysalicylaldehyde derivatives, preferably o-vanillin, and to radiation-resistant formulations comprising solid-state proteins and methoxysalicylaldehyde derivatives, preferably o-vanillin, in combination with Trolox® or isopropanol.

During the process of sterilizing pharmaceutical formulations, especially during terminal sterilization, it is critical that the formulation be protected against incidents detrimental to the activity and/or bioavailability of the active agent or agents comprising the formulation. For solid formulations not easily amenable to sterilization by standard protocols such as sterilizing filtration, alternative methodologies have been developed, including, for example, irradiation. Accordingly, the necessity of protecting certain labile synthetic and biological substrates from the effects of ionizing radiation during the sterilization process is well documented. See, for example, B. D. Reid, PDA J. Pharm. Sci. and Tech., 49 (2), 83–89 (1995), G. P. Jacobs, J. Biomaterials App., 10, 59–95 (1995), and N. G. S. Gopal, Radiat. Phys. Chem., 12, 35–50 (1978).

The methoxysalicylaldehyde derivative o-vanillin, also known as 3-methoxysalicylaldehyde, is a well-known antioxidant that has been employed in a variety of additional contexts, for example, as an enhancer of growth hormone release. See Clark, et al., U.S. Pat. No. 5,015,627.

The compound Trolox®, also known as 6-hydroxy-2,5,7,8-tetramethylchroman-2-carboxylic acid, has also been employed as an anti-oxidant as well as a radioprotectant in various contexts. For example, Trolox® and certain phenolic agents related thereto are useful in protecting solid-state polymers against radiation-induced oxidation. See Soebianto, et al., Polymer Degradation and Stability, 50, 203–210 (1995) and Klemchuk, Radiat. Phys. Chem., 41, 165–172 (1993). This compound has also been employed to ameliorate oxidation in foodstuffs. See, for example, Cort, U.S. Pat. No. 3,986,980. The compound has also been used to promote the repair of amino acid radicals derived from radiolytic protein degradation while in solution. See Bisby, et al., Biochem. Biophys. Res. Comm., 119, 245–251 (1984).

The present invention is directed to prophylactically protecting solid-state proteins from the effects of ionizing radiation by employing either a methoxysalicylaldehyde derivative, preferably 3-methoxysalicylaldehyde, in combination with the protein; a mixture of a methoxysalicylaldehyde derivative, preferably 3-methoxysalicylaldehyde, and 6-hydroxy-2,5,7,8-tetramethylchroman-2-carboxylic acid in combination with the protein; or a mixture of a methoxysalicylaldehyde derivative, preferably 3-methoxysalicylaldehyde and isopropanol, in combination with the protein, prior to exposing the protein to ionizing radiation.

The invention further provides radiation-resistant pharmaceutical formulations comprising a protein and a methoxysalicylaldehyde derivative, preferably 3-methoxysalicylaldehyde; a protein and a combination of a methoxysalicylaldehyde derivative, preferably 3-methoxysalicylaldehyde, and 6-hydroxy-2,5,7,8-tetramethylchroman-2-carboxylic acid; or a protein and a combination of a methoxysalicylaldehyde derivative, preferably 3-methoxysalicylaldehyde and isopropanol.

SUMMARY OF THE INVENTION

The invention provides methods of protecting solid-state proteins from the effects of ionizing radiation which comprise combining the protein with a radiation-protecting amount of a methoxysalicylaldehyde derivative, preferably 3-methoxysalicylaldehyde; radiation-protecting amounts of a methoxysalicylaldehyde derivative, preferably 3-methoxysalicylaldehyde, and 6-hydroxy-2,5,7,8-tetramethylchroman-2-carboxylic acid; or radiation-protecting amounts of a methoxysalicylaldehyde derivative, preferably 3-methoxysalicylaldehyde and isopropanol, prior to exposing the protein to ionizing radiation.

The invention further provides radiation-resistant pharmaceutical formulations comprising a protein and a methoxysalicylaldehyde derivative, preferably 3-methoxysalicylaldehyde; a protein and a combination of a methoxysalicylaldehyde derivative, preferably 3-methoxysalicylaldehyde, and 6-hydroxy-2,5,7,8-tetramethylchroman-2-carboxylic acid; or a protein and a combination of a methoxysalicylaldehyde derivative, preferably 3-methoxysalicylaldehyde and isopropanol.

The invention still further provides compositions comprising a combination of a methoxysalicylaldehyde derivative, preferably 3-methoxysalicylaldehyde, and 6-hydroxy-2,5,7,8-tetramethylchroman-2-carboxylic acid, and for the use of such compositions in pharmaceutical formulations as a radioprotectant.

DETAILED DESCRIPTION OF THE INVENTION

The instant invention provides methods of protecting solid-state proteins from the effects of ionizing radiation which comprise combining the protein, preferably a protein drug, with a radiation-protecting amount of a methoxysalicylaldehyde derivative, preferably 3-methoxysalicylaldehyde; radiation-protecting amounts of a methoxysalicylaldehyde derivative, preferably 3-methoxysalicylaldehyde, and 6-hydroxy-2,5,7,8-tetramethylchroman-2-carboxylic acid; or radiation-protecting amounts of a methoxysalicylaldehyde derivative, preferably 3-methoxysalicylaldehyde and isopropanol, prior to exposing the protein to ionizing radiation.

The invention further provides radiation-resistant pharmaceutical formulations comprising a protein, preferably a protein drug, and a methoxysalicylaldehyde derivative, preferably 3-methoxysalicylaldehyde; a protein, preferably a protein drug, and a combination of a methoxysalicylaldehyde derivative, preferably 3-methoxysalicylaldehyde, and 6-hydroxy-2,5,7,8-tetramethylchroman-2-carboxylic acid; or a protein, preferably a protein drug, and a combination of a methoxysalicylaldehyde derivative, preferably 3-methoxysalicylaldehyde and isopropanol.

The invention still further provides compositions comprising a combination of a methoxysalicylaldehyde derivative, preferably 3-methoxysalicylaldehyde, and 6-hydroxy-2,5,7,8-tetramethylchroman-2-carboxylic acid, and for the use of such compositions in pharmaceutical formulations as a radioprotectant.

As employed throughout the instant description and appendant claims, the term "protein" denotes a macromolecule comprising elongate sequences of amino acids including, but not limited to, peptides, polypeptides, and the like. The term "protein" further embraces any conjugated forms thereof i.e. proteins attached to another molecule or molecules that are not essentially amino acid in nature. Such conjugated proteins may include, but are not limited to, flavoproteins, chromoproteins, hemoglobins, and the like.

As employed throughout the instant description and appendant claims, the term "solid-state protein" embraces any protein macromolecule defined hereinabove which, when at the temperature of irradiation, comprises a solid material, including any hydrated, non-hydrated, or pharmaceutically acceptable salt forms thereof. The term "solid-state protein" further embraces a protein macromolecule defined hereinabove which, when at the temperature of irradiation, comprises a non-solid material (e.g., oils, gelatinous material, and the like), including any hydrated, non-hydrated, or pharmaceutically acceptable salt forms thereof, but when comprising at least a portion of a pharmaceutical formulation, comprises a solid material, or is rendered a solid material by virtue of having been compounded into a pharmaceutical formulation. The term "solid-state protein" still further embraces any solid-state pharmaceutical formulation comprising a protein described hereinabove regardless of whether the protein, or a hydrated, non-hydrated, or pharmaceutically acceptable salt form thereof, is, at the temperature of irradiation, a solid material or a non-solid material.

As employed throughout the instant description and appendant claims, the term "drug" is intended to generically denote anytherapeutant used in the prevention, diagnosis, alleviation, treatment, or cure of a disease or illness, or any similar substance the administration of which is intended to elicit a pharmacologic or physiologic response. According to the methods and pharmaceutical formulations of the invention, the protein preferably comprises a protein drug including, but not limited to, insulin, interferon, collagen, keratin, immunoglobulin, somatotrophin, and the like.

As employed throughout the instant description and appendant claims, the term "ionizing radiation" is intended to mean corpuscular radiation (e.g., neutron or electron, or electromagnetic radiation, e.g. gamma) of sufficient energy to ionize or dissociate molecules into free radicals or electrically charged species, the material being irradiated.

According to the methods of the invention, a solid-state protein, preferably a protein drug, is protected from the effects of ionizing radiation by combining the protein, preferably in the form of a pharmaceutical formulation, with a radiation-protecting amount of a methoxysalicylaldehyde derivative, preferably 3-methoxysalicylaldehyde; with a radiation-protecting amount of a combination of a methoxysalicylaldehyde derivative, preferably 3-methoxysalicylaldehyde, and 6-hydroxy-2,5,7,8-tetramethylchroman-2-carboxylic acid; or with a radiation-protecting amount of a combination of a methoxysalicylaldehyde derivative, preferably 3-methoxysalicylaldehyde, and isopropanol, prior to exposing the protein to ionizing radiation.

Although the protein, preferably a protein drug, may be compounded directly with the methoxysalicylaldehyde derivative, preferably 3-methoxysalicylaldehyde, or the combination of the methoxysalicylaldehyde derivative, preferably 3-methoxysalicylaldehyde and the 6-hydroxy-2,5,7,8-tetramethylchroman-2-carboxylic acid, by simple intimate admixture, it is generally preferred that the protein and the methoxysalicylaldehyde derivative, preferably 3-methoxysalicylaldehyde, or the combination of the methoxysalicylaldehyde derivative, preferably 3-methoxysalicylaldehyde, and the 6-hydroxy-2,5,7,8-tetramethylchroman-2-carboxylic acid, comprise at least a portion of a solid pharmaceutical formulation. In instances where the formulation comprises a protein, a methoxysalicylaldehyde derivative, preferably 3-methoxysalicylaldehyde, and isopropanol, the isopropanol is preferably dispersed in the solid formulation.

Generally, methods of preparing solid pharmaceutical formulations comprising amounts of active ingredients are well known, or will be readily apparent in light of the instant disclosure, to of one of ordinary skill in the art. See, for example,Remington's Pharmaceutical Sciences, Mack Publishing Company, Easton, Pa., 18th Edition (1990).

The solid pharmaceutical formulations of this invention may comprise any conventional solid dosage form including, for example, tablets, pills, capsules, and the like. The formulations may further comprise a binder such as hydroxypropylmethyl cellulose, gum tragacanth, acacia gum, corn starch or gelatin; a disintegrating agent such as corn starch, potato starch, alginic acid, sodium starch gylcolate, croscamellose sodium, or crospovidone; and a sweetening agent such as sucrose, lactose, or saccharin. If desired, the formulations may further comprise lyoprotectants, including, for example, sugars and amino acids, buffers, and stabilizers. Various other materials may be present in the form of coatings or to modify the physical form of the dosage unit. For instance, tablets may be coated with mixtures comprising, for example, titanium dioxide, dextrose, polyethylene glycol, sodium carboxymethyl cellulose, dextrin, and the like. The coatings may also comprise the form of an enteric polymer including phthalate derivatives, such as cellulose acetate phthalate, polyvinylacetate phthalate and hydroxypropylmethyl cellulose phthalate, polyacrylic acid derivatives, such as methacrylic acid copolymer, vinyl acetate, and crotonic acid copolymers.

In the pharmaceutical formulations of the instant invention, the methoxysalicylaldehyde derivative, preferably 3-methoxysalicylaldehyde, generally comprises at least about 0.1% by weight of the formulation, the 6-hydroxy-2,5,7,8-tetramethylchroman-2-carboxylic acid generally comprises at least about 0.1% by weight of the formulation, and the isopropanol comprises at least about 0.1% of the formulation. Preferably, the methoxysalicylaldehyde derivative, preferably 3-methoxysalicylaldehyde, comprises from about 2.9% to about 8.0% by weight of the formulation, the 6-hydroxy-2,5,7,8-tetramethylchroman-2-carboxylic acid comprises from about 0.1% to about 1.0% by weight of the formulation, and the isopropanol comprises from about 0.1% to about 4.0% of the formulation. These percent by weight ranges may, of course, be varied somewhat according to the substance to be protected as will be recognized by one of ordinary skill in the art in view of the instant disclosure.

Experimental

The ability of a methoxysalicylaldehyde derivative, preferably 3-methoxysalicylaldehyde; or a combination of a methoxysalicylaldehyde derivative, preferably 3-methoxysalicylaldehyde and 6-hydroxy-2,5,7,8-tetramethylchroman-2-carboxylic acid; or a combination of a methoxysalicylaldehyde derivative, preferably 3-methoxysalicylaldehyde and isopropanol, to protect solid-state proteins from the effects of ionizing radiation may be demonstrated according to the following experimental protocols, the results of which are illustrated in tabular form in Tables 1 to 4 shown hereinbelow.

Protection of Solid-State Proteins Using 3-methoxysalicylaldehyde

Porcine somatotrophin (pST) (Monsanto; St. Louis, Mo.) was dissolved in pH 9.5 buffer at 75 g/l, diafiltered using 6 volumes of pH 9.5 water, and refrigerated overnight. The compound 3-methoxysalicylaldehyde (99%; Sigma Chemical Co.; St. Louis, Mo.), a combination of 3-methoxysalicylaldehyde and 6-hydroxy-2,5,7,8-tetramethylchroman-2-carboxylic acid (97%; Aldrich Chemical Co.; Milwaukee, Wis.), or a combination of 3-methoxysalicylaldehyde and isopropanol, was added to the solution in an amount sufficient to obtain the desired concentration. Upon addition of the 3-methoxysalicylaldehyde, the pH decreased and, when the pH had reached 7.5, the solution was titrated with sodium hydroxide such that this pH was maintained. Sucrose was added to facilitate the pelleting process. The solutions were lyophilized in trays by freezing at −45° C. followed by vacuum drying at a shelf temperature of 15° C. for ~15 hours at a depth of 0.4 to 1 cm and 100 militorr vacuum.

Formulation pellets were manufactured by grinding gently the bulk material prepared as described hereinabove into a powder using a mortar and pestle. Magnesium stearate (0.5%) was mixed into the formulations for 3 minutes in a shaker. The resulting material was compressed at 15,000 lbs. pressure into one-inch diameter slugs using a press. The slugs were broken, ground gently, and the resulting granulation was screened through a wire mesh (sieve #20). One-eighth inch diameter pellets of uniform length and hardness were then produced and pellets within ±7% of the target weight were selected.

The test pellets were then subjected to an electron beam (e-beam) to radiation doses of 25 and 60 kGy at ambient temperature.

Analysis of Formulations for Protein Degradation

A reverse phase high performance liquid chromatography (RP-HPLC) system was used to monitor pST degradation following irradiation. HPLC was performed on a Waters Alliance System (Waters Instrument Co.; Milford, Mass.) with a UV detector set at 220 nm and a Symmetry 300 C-18 column (Waters Instrument Co.; Milford, Mass.). A gradient elution method was employed (Mobile Phase A: 0.1% TFA, 1% IPA in deionized water; and Mobile Phase B: 0.065% TFA, 1% IPA, 88% acetonitrile in deionized water). Approximately 5 mg of the irradiated solid formulation was dissolved in Mobile Phase B in a 10 ml volumetric flask and monitored forpST degradation. The gradient employed to monitor pST degradation was programmed as follows: Mobile Phase A: Mobile Phase B; 70:30 from 0 to 6.0 minutes at a flow rate of 1.0 ml/minute, switched to 50:50 from 6.0 to 6.1 minutes at a flow rate of 1.0 ml/minute, switched to 32:68 from 6.1 to 78.0 minutes at a flow rate of 1.0 ml/minute, then switched to 70:30 from 78.0 to 78.1 minutes at a flow rate of 1.0 ml/minute, finally followed by a flow rate of 2.0 ml/minute from 78.1 to 78.5 minutes.

The area-under-the-peak was determined for a main peak for the irradiated (Si) and non-irradiated (S0) samples, and the fraction of the remaining pST, f, was calculated as f=(Si/mi)/(S0/m0), where mi and m0 represent the weights of the solids (in mg) employed for the solution preparation.

Discussion

As depicted hereinbelow in Table 1, the combination of the protein and 3-methoxysalicylaldehyde (denoted hereinbelow in Tables 1 to 3 as "o.v.") resulted in an increased level of protein stability to irradiation that was directly related to the concentration of the 3-methoxysalicylaldehyde.

Similarly, as depicted hereinbelow in Tables 2 and 3, the combination of the protein and the 3-methoxysalicylaldehyde/6-hydroxy-2,5,7,8-tetramethylchroman-2-carboxylic acid (denoted hereinbelow in Tables 2 and 3 as "Trolox®") also resulted in an increased level of protein stability to irradiation.

As depicted in Table 4, the combination of the protein and the 3-methoxysalicylaldehyde/isopropanol also resulted in an increased level of protein stability to irradiation that was directly related to the concentrations of both the 3-methoxysalicylaldehyde and the isopropanol.

TABLE 1

Impact of o.v. on pST irradiated at 60 kGy

| o.v. (wt %) | % pST monomer remaining after irradiation |
|---|---|
| 0 | 54.2 |
| 2.9 | 64.6 ± 0.2 |
| 5.7 | 72.4 |
| 8.0 | 75.7 ± 0.8 |

TABLE 2

Impact of o.v. and Trolox ® on pST irradiated at 25 kGy

| o.v. (wt %) | Trolox ® (wt %) | % pST monomer remaining after irradiation |
|---|---|---|
| 0 | 0 | 79.4 |
| 0 | 0.4 | 73.3 |
| 8.0 | 0 | 82.9 |
| 8.0 | 0.4 | 88.1 |

TABLE 3

Impact of o.v. and Trolox ® on pST irradiated at 60 kGy

| o.v. (wt %) | Trolox ® (wt %) | % pST monomer remaining after irradiation |
|---|---|---|
| 0 | 0 | 54.2 |
| 0 | 0.4 | 52.2 ± 0.4 |
| 2.9 | 0 | 64.5 |
| 2.9 | 0.4 | 67.7 |
| 2.9 | 1 | 67.0 |
| 2.9 | 2 | 62.7 |
| 8.0 | 0 | 75.7 ± 0.8 |
| 8.0 | 0.4 | 78.8 ± 0.1 |

TABLE 4

Impact of o.v. and isopropanol (IPA) on pST irradiated at 60 kGy

| o.v. (wt %) | % IPA* | % pST monomer remaining after irradiation |
|---|---|---|
| 0 | 0 | 54.2 |
| 2.9 | 0 | 64.5 |
| 2.9 | 1.0 | 67.1 |

TABLE 4-continued

Impact of o.v. and isopropanol (IPA) on pST irradiated at 60 kGy

| o.v. (wt %) | % IPA* | % pST monomer remaining after irradiation |
|---|---|---|
| 2.9 | 1.7 | 67.4 |
| 2.9 | 3.1 | 68.7 |

*determined by gas chromatography

What is claimed is:

1. A method of protecting a solid-state protein from ionizing radiation which comprises combining said protein with a radiation-protecting amount of a 3-methoxysalicylaldehyde prior to exposing said protein to said ionizing radiation.

2. A method of protecting a solid-state protein from ionizing radiation which comprises combining said protein with radiation-protecting amounts of a methoxysalicylaldehyde and 6-hydroxy-2,5,7,8-tetramethylchroman-2-carboxylic acid prior to exposing said protein to said ionizing radiation.

3. A method according to claim 2 wherein said methoxysalicylaldehyde is 3-methoxysalicylaldehyde.

4. A method of protecting a solid-state protein from ionizing radiation which comprises combining said protein with radiation-protecting amounts of a methoxysalicylaldehyde and isopropanol prior to exposing said protein to said ionizing radiation.

5. A method according to claim 4 wherein said methoxysalicylaldehyde is 3-methoxysalicylaldehyde.

6. A formulation comprising a solid-state protein and 3-methoxysalicylaldehyde.

7. A formulation according to claim 6 wherein said protein is a drug.

8. A formulation according to claim 6 wherein said methoxysalicylaldehyde comprises at least about 0.1% by weight of said formulation.

9. A formulation according to claim 8 wherein said methoxysalicylaldehyde comprises from about 2.9% to about 8.0% by weight of said formulation.

10. A formulation comprising a solid-state protein, a methoxysalicylaldehyde, and 6-hydroxy-2,5,7,8-tetramethylchroman-2-carboxylic acid.

11. A formulation according to claim 10 wherein said protein is a drug.

12. A formulation according to claim 10 wherein said methoxysalicylaldehyde is 3-methoxysalicylaldehyde.

13. A formulation according to claim 10 wherein said methoxysalicylaldehyde comprises at least about 0.1% by weight of said formulation, and said 6-hydroxy-2,5,7,8-tetramethylchroman-2-carboxylic acid comprises at least about 0.1% by weight of said formulation.

14. A formulation according to claim 13 wherein said methoxysalicylaldehyde comprises from about 2.9% to about 8.0% by weight of said formulation, and said 6-hydroxy-2,5,7,8-tetramethylchroman-2-carboxylic acid comprises from about 0.1% to about 1.0% by weight of said formulation.

15. A formulation comprising a solid-state protein, methoxysalicylaldehyde, and isopropanol.

16. A formulation according to claim 15 wherein said protein is a drug.

17. A formulation according to claim 15 wherein said methoxysalicylaldehyde is 3-methoxysalicylaldehyde.

18. A formulation according to claim 15 wherein said methoxysalicylaldehyde comprises at least about 0.1% by weight of said formulation, and said isopropanol comprises at least about 0.1% of said formulation.

19. A formulation according to claim 15 wherein said methoxysalicylaldehyde comprises from about 2.9% to about 8.0% by weight of said formulation, and said isopropanol acid comprises from about 0.1% to about 4.0% of said formulation.

20. A composition comprising a methoxysalicylaldehyde and 6-hydroxy-2,5,7,8-tetramethylchroman-2-carboxylic acid.

21. A composition according to claim 20 wherein said methoxysalicylaldehyde is 3-methoxysalicylaldehyde.

* * * * *